United States Patent [19]

Takhar et al.

[11] Patent Number: 5,716,850

[45] Date of Patent: Feb. 10, 1998

[54] MONITORING THE COLOUR AND BITTERNESS OF BEER

[75] Inventors: Gurinder Takhar, Derby; Mandy King, Bedfordshire, both of United Kingdom

[73] Assignee: Whitbread PLC, London, United Kingdom

[21] Appl. No.: 687,557

[22] PCT Filed: Feb. 3, 1995

[86] PCT No.: PCT/GB95/00219

§ 371 Date: Sep. 16, 1996

§ 102(e) Date: Sep. 16, 1996

[87] PCT Pub. No.: WO95/21242

PCT Pub. Date: Aug. 10, 1995

[30] Foreign Application Priority Data

Feb. 7, 1994 [GB] United Kingdom ........... 9402304.1

[51] Int. Cl.⁶ .................................................. G01N 33/14
[52] U.S. Cl. ................... 436/24; 250/458.1; 250/459.1;
250/910; 356/317; 356/318; 356/417; 426/231;
436/131; 436/132; 436/172; 422/82.05;
422/82.06; 422/82.07; 422/82.08
[58] Field of Search ..................... 250/458.1, 459.1,
250/910; 356/317, 318, 417; 436/24, 131,
132, 172; 426/231; 422/82.05, 82.06, 82.07,
82.08

[56] References Cited

U.S. PATENT DOCUMENTS 3,615,660  10/1971  Bavisotto ........................... 99/50.5
4,751,185   6/1988  Ono et al. ........................... 436/24
4,767,640   8/1988  Goldstein et al. ................. 426/600
5,272,090  12/1993  Gavish et al. ..................... 436/133

FOREIGN PATENT DOCUMENTS 0 564 157 A1  3/1993  European Pat. Off. .

OTHER PUBLICATIONS

Tomlinson et al "A Novel Method for Bitterness Determination in Beer Using a Delayed Fluorescence Technique", Mar. 1995.
J. Inst. Brew. Mar.–Apr. 1995, vol. 101, pp. 113–118.
Sendra, Jose M. et al., "Determination of β–Glucan in Wort and Beer By Its Binding With Calcofluor, Using a Fluorimetric Flow–Injection–Analysis (FIA) Method," *Inst. Brew.*, Sep.–Oct., 1989, vol. 95, pp. 327–332.
Sharpe, F.R., et al., "The Measurement of Beer and Wort Colour—A New Approach," *Inst. Brew.*, Jul.–Aug., 1992, vol. 98, pp. 321–324.

*Primary Examiner*—Jill Warden
*Assistant Examiner*—Sharidan Carrillo
*Attorney, Agent, or Firm*—Sughrue, Mion, Zinn, Macpeak & Seas, PLLC

[57] ABSTRACT

A method of determining one or both of the colour and bitterness of beer by illuminating the beer with light of a pre-determined wavelength, typically 400±30 nm, to cause iso-α-acids in the beer to fluoresce. The fluorescence is detected over a range of wavelengths, typically 420 to 673 nm, using a fluorescence spectrophotometer. One or both of the colour and bitterness of the beer is determined by comparing an output signal from the fluorescence spectrophotometer to output signals stored for beers of known colour and bitterness.

18 Claims, 2 Drawing Sheets

BEER FLOW

BEER FLOW

MONITORING THE COLOUR AND BITTERNESS OF BEER

FIELD OF INVENTION

In beer production, it is desirable to ensure that the beer produced has a consistent colour and a consistent taste. To achieve this, it is necessary to monitor both the colour and taste of the beer to ensure it is within acceptable limits.

DISCUSSION OF PRIOR ART

Various methods for measuring the colour of beer are discussed in the paper "The Measurement of Beer and Wort Colour—A New Approach" by Sharpe et al, Journal of the Institute of Brewing, 1992, volume 98, pages 321–324. As described in this paper, the conventional way to measure the colour of beer is using colour glass comparator discs, and to assess the colour by direct visual comparison with these discs. The colour temperature of the illuminant can vary how colour is perceived, and accordingly a standard illuminant is required when using comparator discs. Ageing of the coloured discs and incorrect storage can also cause colour shifts which effect the determination of colour, and the range of disc colours, whilst being wide, tend not to match the exact colour of the beer, for example the yellowness of lager or the brownness of ales and bitters. Further still, the comparison is subjective, and as it is totally manual there may be some inconsistency as the person monitoring the colour becomes fatigued, and additionally between different breweries, and even within the same brewery, with different people carrying out the monitoring.

Some of these problems are overcome by using a spectrophotometric method of measuring. Such a method has been approved by the Institute of Brewing, the European Brewery Convention, and the American Society of Brewing Chemists, all of which recommend the use of a single wavelength spectrophotometric measurement at 430 nm. In such systems, light of 430 nm illuminates the beer sample, and the absorption of light by the beer is determined. From the absorption, the colour is calculated. This system is not suitable for analysis of worts from coloured malts, dark malts or roasted barley which absorb too much light. Further still this system is error prone due to back scattered light from particles suspended in the beer creating a slight haze.

The approach suggested in the above paper is to use a tristimulus method to determine the colour of beer. In this method the beer is illuminated with light of three different wavelength ranges to determine the hue or actual colour, the value, lightness or darkness of the colour, and chroma, vividness or dullness. This system is more accurate than either the use of comparator discs or single wavelength spectrophotometric methods. Use of illumination in each of three different wavelength ranges ensures that the colour of hazy beers and worts are accurately monitored and not falsely assessed as with the single wavelength method, and the resulting assessment is similar to that of the human eye.

The bitterness of beer has conventionally been determined by a taster sampling the beer. Again, such measurements are subjective, and so vary between breweries, and within breweries as the taster becomes fatigued.

The bitterness in beer is largely determined by α-acids, which are resinous constituents of the hops, as they undergo an isomerisation reaction to produce iso-α-acids. The iso-α-acids account for about 70% of the bitterness of beer. A method of determining the bitterness in the laboratory has been developed in which a sample is taken of the beer, and this is acidified. The acidified beer sample is illuminated with ultra-violet light at a wavelength of 275 nm, and the absorption of this light by the sample is measured. The bitterness of the beer is calculated by monitoring its absorption of ultra-violet light.

SUMMARY OF THE INVENTION

According to the present invention, a method of determining one or both of the colour and bitterness of beer comprises the steps of illuminating the beer with light of a predetermined wavelength to cause iso-α-acids in the beer to fluoresce, detecting the fluorescence over a range of wavelengths using a fluorescence spectrophotometer, and determining one or both of the colour and bitterness of the beer by comparing an output signal from the fluorescence spectrophotometer to output signals stored for beers of known colour and bitterness.

The advantage of the present invention is that the colour and bitterness of beer can be determined, without requiring the subjective assessment of a person, and without requiring a sample of beer to be acidified. This may also be performed in-line, rather than requiring a sample to be removed from the beer. With an in-line system, it is possible to control the blending of beer to give a desired colour and bitterness combination.

Preferably, the beer is illuminated with light at a wavelength of 400 nm, and the fluorescence emission spectrum is measured over the range 420 to 673 nm.

Preferably, optical fibres are used to introduce light into the beer, and to transmit the emitted light from the beer to the fluorescence spectrophotometer. This ensures minimum light loss in the system. A prism may be used to deflect light to pass through the beer, and to deflect the emitted light along the optical fibre, however it is preferred that a fibre optic tip is used. In either case, the fibre optic tip or the prism are preferably located in the actual beverage, for example in a flow line carrying the beer, or in a vat. Preferably, the fluorescence emission spectrum of the beer is applied to a computer which determines parameters of the fluorescent intensity using regression analysis techniques. The parameters are compared with parameters for samples of known colour and bitterness to determine the colour and/or bitterness of the beer under test. A linear regression calculation is suitable to determine parameters relating to the colour of the beer, however preferably a principal component regression calculation is used for determination of the colour and bitterness of the beer.

BRIEF DESCRIPTION OF THE DRAWINGS

An example of the present invention will be described in accordance with the accompanying drawings in which.

DETAILED DESCRIPTION OF PREFERRED EMBODIMENTS

The bitter taste of beer is primarily due to iso-α-acids which are derived from α-acids present in hops as they undergo an isomerisation reaction. An iso-α-acid has an acyclic molecule containing delocalised pi-electrons, and three hydroxyl groups. It is believed that this structure leads to the iso-α-acid fluorescing when excited with a particular wavelength of light. A pre-isomerised beer extract is irradiated with visible light at a wavelength of 400 nm (±30 nm) and in response to this excitation, the α-acids emit light over the wavelength range of 420 to 673 nm. The fluorescent intensity (Pf) is the product of the quantum yield of fluorescence (φf) and the radiant power absorbed by the sample.

$$Pf = \phi f(Po - P) \quad (1)$$

where:

$$\phi f = \frac{\text{photons emitted as fluorescence}}{\text{photons absorbed by sample}} \quad (2)$$

Not all of the emitted photons will be detected as some will be absorbed. The absorption, A, is given by Beer Lamberts law as:

$$A = Ebc = \log_e\left(\frac{Po}{P}\right) \quad (3)$$

Where

E=molar absorbtivity of the sample
b=path length
c=concentration of the sample

By compensating for the absorption of photons by the beer, equation 1 becomes:

$$Pf = \phi f.Po.(1 - e^{-A}) \quad (4)$$

This equation indicates an exponential relationship between absorption and fluorescence intensity. Colour is related to the absorption.

Accordingly, if the colour is known it is possible to determine the concentration of iso-α-acids in the pre-isomerised extract from the fluorescence emission spectrum. Alternatively, by comparing the fluorescence intensity over a range of wavelengths with that obtained from beer samples having a known bitterness and colour, it is possible to determine the beer bitterness and colour from one set of experimental observations.

Figure 1:
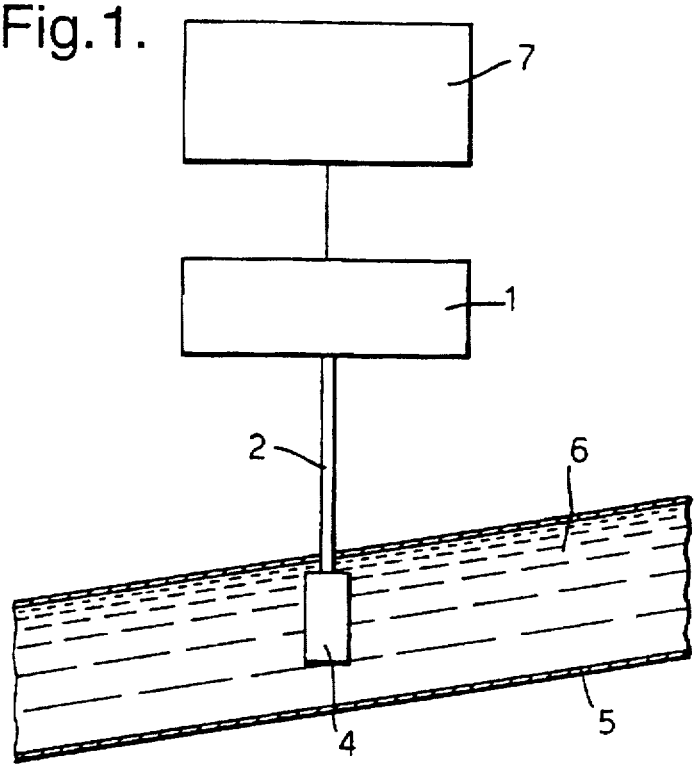
FIG. 1 shows an apparatus for determining the colour and bitterness of beer in-line.
Figure 2:
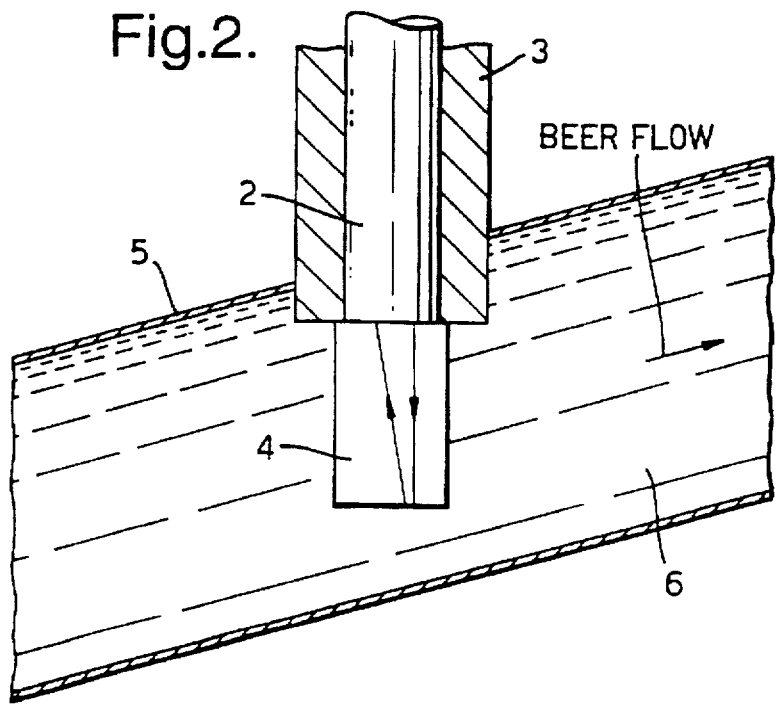
FIG. 2 shows an enlarged view of a first example of the fibre optic probe shown in FIG. 1.
Figure 3:
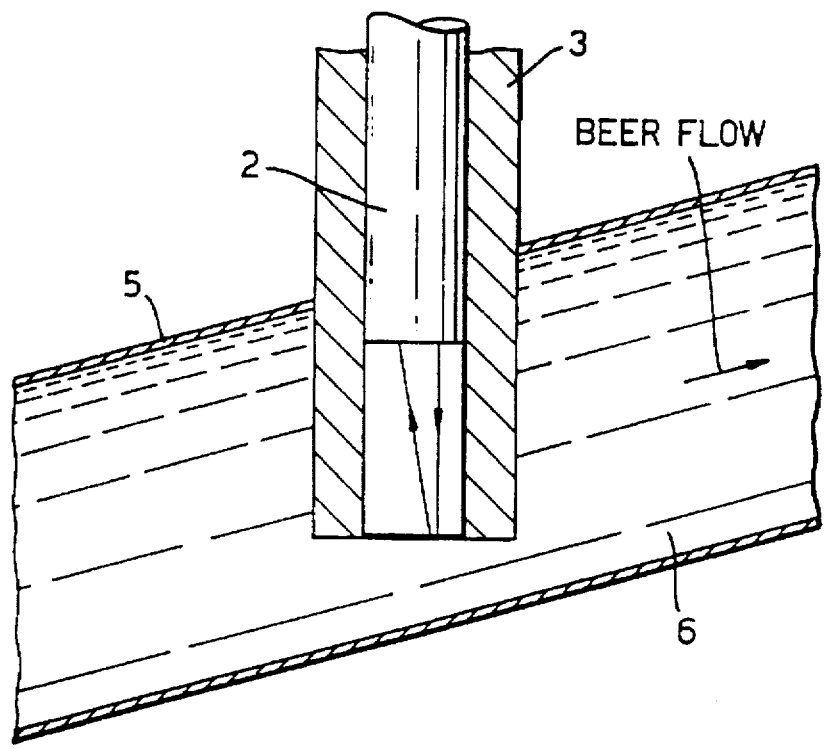
FIG. 3 shows an enlarged view of a second example of the fibre optic probe shown in FIG. 1; and, FIG. 4 shows a schematic diagram of a laboratory measurement system according to the present invention.

As shown in FIGS. 1 to 3, for an in-line system, the fluorescence emission spectrum is determined by providing a fluorescence spectro-photometer 1 which emits light at a wavelength of 400 nm (±30 nm) along a fibre optic cable 2. The fibre optical cable 2 is housed in a stainless steel casing 3 which can be easily and hygienically cleaned. As shown in FIG. 2, a quartz prism 4 is included at the end of the fibre optic cable 2, and the prism 4 is inserted into a pipe line 5 carrying beer 6 to be sampled. The prism 4 has a path length of 10 to 20 mm. Alternatively, as shown in FIG. 3, a fibre optic tip can be used in place of the prism 4. Light from the fluorescence spectro-photometer 1 is passed to the prism 4 or tip via the fibre optical cable, and illuminates the beer 6 in the pipe line 5. The beer flows at an acute angle to the prism 4 or tip. The beer 6 emits light which passes through the prism 4 or tip to the fibre optic cable 2. The light emitted by the beer 6 passes to the fluorescence spectrophotometer 1 via the fibre optic cable 2. The fluorescence spectrophotometer 1 outputs a signal corresponding to the fluorescent emission spectrum of the beer 6. The signal is input to a computer 7, for example along an RS232 link, and the computer determines parameters of the emission spectrum, and determines the colour and bitterness of the beer 6 by comparison of these parameters with those of known calibration samples.

The comparison between results from known calibration samples and a sample under test is achieved by applying regression algorithms to the fluorescence emission spectrum. Either a linear multiple regression or a principal component regression, for example using a chemometric package such as Perkin Elmer's PC Quant software or Camo AS's "The Unscrambler" (TRADEMARK) is used to determine a parameter indicative of the colour and a parameter indicative of the bitterness of the sample when compared to known calibration samples.

Figure 4:
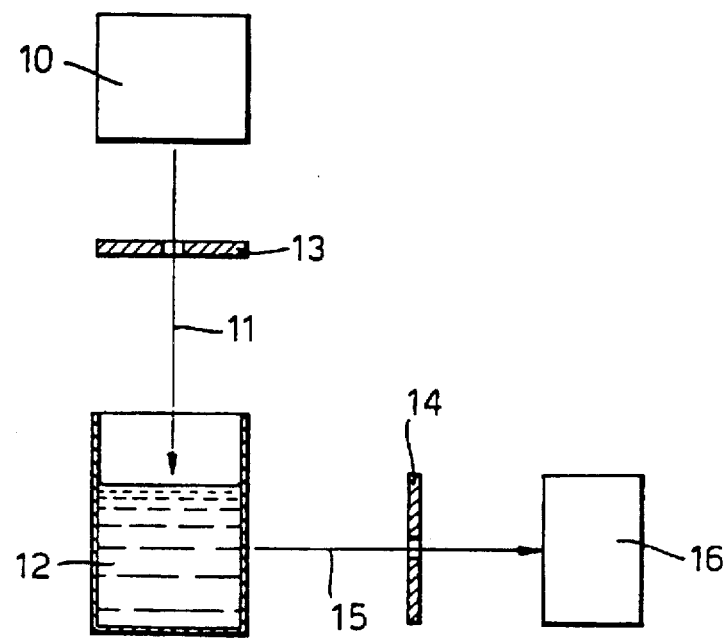

FIG. 4 shows a schematic diagram of a laboratory system for measuring colour and bitterness. A xenon lamp (10) is used to provide excitation radiation (11) to a sample of beer (12) removed from a process line. The radiation passes through a slit (13). The radiation (11) causes iso-α-acid in the beer (12) to fluoresce. The fluoresced light (15) is detected by an emission monochromator including a photomultiplier tube (16) and a slit (14). The colour and bitterness are determined using a chemometric package as with the in-line system. In this case, the detection is by transmission fluorescence, rather than by front face fluorescence as for the in-line system.

We claim:

1. A method of determining one or both of the colour and bitterness of beer comprising the following steps:
   illuminating α-acids in the beer to fluoresce;
   detecting the fluorescence over a range of wavelengths using a fluorescence spectrophotometer; and
   determining one or both of the colour and bitterness of the beer by comparing an output signal of the α-acids from the fluorescence spectrophotometer to stored α-acid output signals for beers of known colour and bitterness.

2. A method according to claim 1, in which the beer is illuminated with light at a wavelength of at least 400 (±30) nm.

3. A method according to claim 1, in which a fluorescence emission spectrum is measured over a range of 420 to 673 nm.

4. A method according to claim 1, wherein said illuminating step comprises introducing light into the beer with optical fibres, and said detecting step comprises transmitting emitted light from the beer to the fluorescence spectrophotometer via said optical fibres.

5. A method according to claim 4, in which a prism is used to deflect light to pass through the beer, and to deflect the emitted light along the optical fibre.

6. A method according to claim 4, in which a fibre optic tip is used to deflect light to pass through the beer, and to deflect the emitted light along the optical fibre.

7. A method according to claim 5, in which the prism is located in the beer.

8. A method according to claim 3, in which a computer calculates fluorescent intensity of the fluorescence emission spectrum of the beer using regression analysis techniques.

9. A method according to claim 1, wherein said determining step comprises using a linear regression calculation to determine parameters relating to the colour of the beer.

10. A method according to claim 1, wherein said determining step comprises using a principal component regression calculation to determine the colour and bitterness of the beer.

11. A method according to claim 2, in which a fluorescence emission spectrum is measured over a range of 420 to 673 nm.

12. A method according to claim 2, wherein said illuminating step comprises introducing light into the beer with optical fibres, and said detecting step comprises transmitting emitted light from the beer to the fluorescence spectrophotometer via said optical fibres.

13. A method according to claim 12, in which a prism is used to deflect light to pass through the beer, and to deflect the emitted light along the optical fibre.

14. A method according to claim 12, in which a fibre optical tip is used to deflect light to pass through the beer, and to deflect the emitted light along the optical fibre.

15. A method according to claim 13, in which the prism is located in the beer.

16. A method according to claim 14, in which the fibre optic tip is located in the beer.

17. A method according to claim 6, in which the fibre optic tip is located in the beer.

18. A method according to claim 11, in which a computer calculates fluorescent intensity of the fluorescence emission spectrum of the beer using regression analysis techniques.

* * * * *